United States Patent [19]

Curro et al.

[11] Patent Number: 5,700,255
[45] Date of Patent: Dec. 23, 1997

[54] ABSORBENT ARTICLE HAVING COMPOSITE ELASTICIZED MEMBER

[75] Inventors: John Joseph Curro; Scot G. Wolf, both of Cincinnati; Willie King, Wyoming, all of Ohio

[73] Assignee: The Procter & Gamble Company, Cincinnati, Ohio

[21] Appl. No.: 747,427

[22] Filed: Nov. 20, 1996

Related U.S. Application Data

[63] Continuation of Ser. No. 112,014, Aug. 25, 1993, abandoned.

[51] Int. Cl.$^6$ .................................................. A61F 13/15
[52] U.S. Cl. ........................ 604/385.2; 604/385.1; 604/358
[58] Field of Search ....................... 604/385.1, 385.2, 604/358, 383, 369, 373

[56] References Cited

U.S. PATENT DOCUMENTS

| | | | |
|---|---|---|---|
| 3,949,742 | 4/1976 | Nowakowski | 128/155 |
| 4,228,600 | 10/1980 | Krug et al. | 36/32 R |
| 4,342,314 | 8/1982 | Radel et al. | 128/287 |
| 4,381,781 | 5/1983 | Sciaraffa et al. | 604/372 |
| 4,606,964 | 8/1986 | Wideman | 428/152 |
| 4,695,422 | 9/1987 | Curro et al. | 264/504 |
| 4,720,415 | 1/1988 | Vander Wielen et al. | 428/152 |
| 4,834,741 | 5/1989 | Sabee | 604/385.2 |
| 4,839,216 | 6/1989 | Curro et al. | 428/134 |
| 4,857,067 | 8/1989 | Wood et al. | 604/389 |
| 4,863,779 | 9/1989 | Daponte | 428/152 |
| 5,143,679 | 9/1992 | Weber et al. | 264/288.8 |
| 5,151,092 | 9/1992 | Buell et al. | 604/385.2 |
| 5,156,793 | 10/1992 | Buell et al. | 264/288.8 |
| 5,167,897 | 12/1992 | Weber et al. | 264/288.8 |
| 5,196,000 | 3/1993 | Clear et al. | 604/385.2 |
| 5,221,274 | 6/1993 | Buell et al. | 604/385.2 |
| 5,234,423 | 8/1993 | Alemmy et al. | 604/385.2 |
| 5,275,590 | 1/1994 | Huffman et al. | 604/385.1 |
| 5,330,458 | 7/1994 | Buell et al. | 604/385.1 |
| 5,464,401 | 11/1995 | Hasse et al. | 604/385.1 |

FOREIGN PATENT DOCUMENTS

| | | | |
|---|---|---|---|
| 0551925 | 7/1993 | European Pat. Off. | 604/385.2 |
| 2 258 840 | 2/1993 | United Kingdom . | |

*Primary Examiner*—David H. Willse
*Assistant Examiner*—Dennis Ruhl
*Attorney, Agent, or Firm*—Kevin C. Johnson; William Scott Andes; E. Kelly Linman

[57] ABSTRACT

Absorbent article such as disposable diapers, incontinent briefs, diaper holders, and the like, that have a unique composite member forming a portion of the elasticized side panel and the elasticized waistband. The composite member includes an elastomeric member and a three-dimensional, macroscopically expanded, formed-film member secured to at least one of the surfaces of the elastomeric member. The composite member provides the preferred bulk, elasticity, resiliency, and stiffness required to withstand the application, wear and removal stresses and provide the desired comfort during the typical wearing cycle of a disposable diaper.

19 Claims, 4 Drawing Sheets

ABSORBENT ARTICLE HAVING COMPOSITE ELASTICIZED MEMBER

CROSS-REFERENCE TO RELATED APPLICATION

This application is a continuation of application Ser. No. 08/112,014, filed Aug. 25, 1993 now abandoned.

FIELD OF THE INVENTION

The present invention relates to absorbent articles such as diapers, incontinent briefs, diaper holders, and the like, and more particularly, to absorbent articles having a composite elasticized member. The composite elasticized member is preferably used as a portion of the elasticized side panel and/or the elasticized waistband of the absorbent article.

BACKGROUND OF THE INVENTION

Infants and other incontinent individuals wear absorbent articles such as diapers to receive and contain urine and other body exudates. Absorbent articles function to both contain the discharged materials and to isolate these materials from the body of the wearer and from the wearer's garments and bed clothing. Disposable absorbent articles having many different basic designs are known to the art. For example, U.S. Pat. No. Re. 26,152 issued to Duncan and Baker on Jan. 31, 1967, describes a disposable diaper which has achieved wide acceptance and commercial success. U.S. Pat. No. 3,860,003 issued to Buell on Jan. 14, 1975, describes an elasticized leg cuff disposable diaper which has achieved wide acceptance and commercial sucess.

However, absorbent articles have a tendency to sag or gap away from and to slide/slip down on the body of the wearer during wear. This sagging/gapping and sliding/slipping is caused by the relative motions of the wearer as the wearer breaths, moves and changes positions, by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer in the waste region and the leg regions of the absorbent article.

In order to provide a more comfortable and contouring fit certain commercially available absorbent articles have been provided with elastic waist features and elasticized side panels. An example of a disposable diaper with an elastic waist feature which has achieved wide acceptance and commercial success is disclosed in U.S. Pat. No. 4,515,595 issued Kievit et al. on May 7, 1985. An example of a disposable diaper with elasticized side panels positioned in the ears (ear flaps) of the diaper is disclosed in U.S. Pat. No. 4,857,067 issued to Wood, et al. on Aug. 15, 1989. In order for the elastic waist feature and the elasticized side panel to perform appropriately they must have certain characteristics. It is important for the elastic waist feature and the elasticized side panels to be of sufficient bulk to provide a cushioning effect which has an increased comfort and improved fit for the wearer. In addition, it is preferable that they be of sufficient stiffness and resilience such that the waist and ear portions of the diaper maintain their shape during application and use of the diaper. That is, the waist and ear portions of the diaper should stand on their own and should not flop over due to the weight of the material forming the waist feature and side panel member. In addition, they must also have a certain degree of elasticity in order that they may move and stretch so that they conform with the body of the wearer during use.

SUMMARY OF THE INVENTION

The present invention provides absorbent articles such as disposable diapers, incontinent briefs, diaper holders and the like, that have a unique composite member. Such absorbent articles comprise a containment assembly preferably comprising a liquid pervious topsheet, a liquid impervious backsheet joined with the topsheet, and an absorbent core positioned between the topsheet and the backsheet. The absorbent core has side edges and waist edges. A composite elastic member extends laterally outward from at least one of the side edges of the absorbent core to form a portion of the elasticized side panel. The composite member includes an elastomeric member having a first surface and a second surface and a three-dimensional, macroscopically expanded, formed-film secured to the first surface of the elastomeric member.

In a preferred embodiment the composite member includes a three-dimensional, macroscopically expanded, formed-film secured to the second surface of the elastomeric member. Alternatively, the composite member includes a nonwoven web secured to the second surface of the elastomeric member.

The elasticized side panel preferably comprises a portion of the backsheet, a portion of the topsheet, and the composite member.

Preferably, a composite elastic member extends longitudinally outward from at least one of the waist edges of the absorbent core to form a portion of the elasticized waistband. The composite member includes an elastomeric member having a first surface and a second surface and a three-dimensional, macroscopically expanded, formed-film secured to the first surface of the elastomeric member.

In a preferred embodiment the composite member includes a three-dimensional, macroscopically expanded, formed-film secured to the second surface of the elastomeric member. Alternatively, the composite member includes a nonwoven web secured to the second surface of the elastomeric member.

The elasticized waistband preferably comprises a portion of the backsheet, a portion of the topsheet, and the composite member.

The term "macroscopically expanded", as used herein refers to webs, ribbons and films which have caused to conform to the surface of a three-dimensional forming structure so that both surfaces thereof exhibit a three-dimensional pattern of surface aberrations corresponding to the macroscopic cross-section of the forming structure, the surface aberrations comprising patterns being individually discernible to the normal naked eye, i.e., a normal eye having 20/20 vision unaided by any instrument that changes the appearance, size or distance of an object or otherwise alters the visual powers of the eye, when the perpendicular distance between the viewer's eye and the plane of the web is about 12 inches. Such macroscopically expanded webs, ribbons and films are typically caused to conform to the surface of the forming structure by embossing, i.e., when the forming structure exhibits a pattern comprised primarily of male projections by debossing, i.e., when the forming structure exhibits a pattern comprised of primarily of female capillary networks, or by extrusion of a resinous melt directly onto the surface of a forming structure of either type.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

Figure 1:
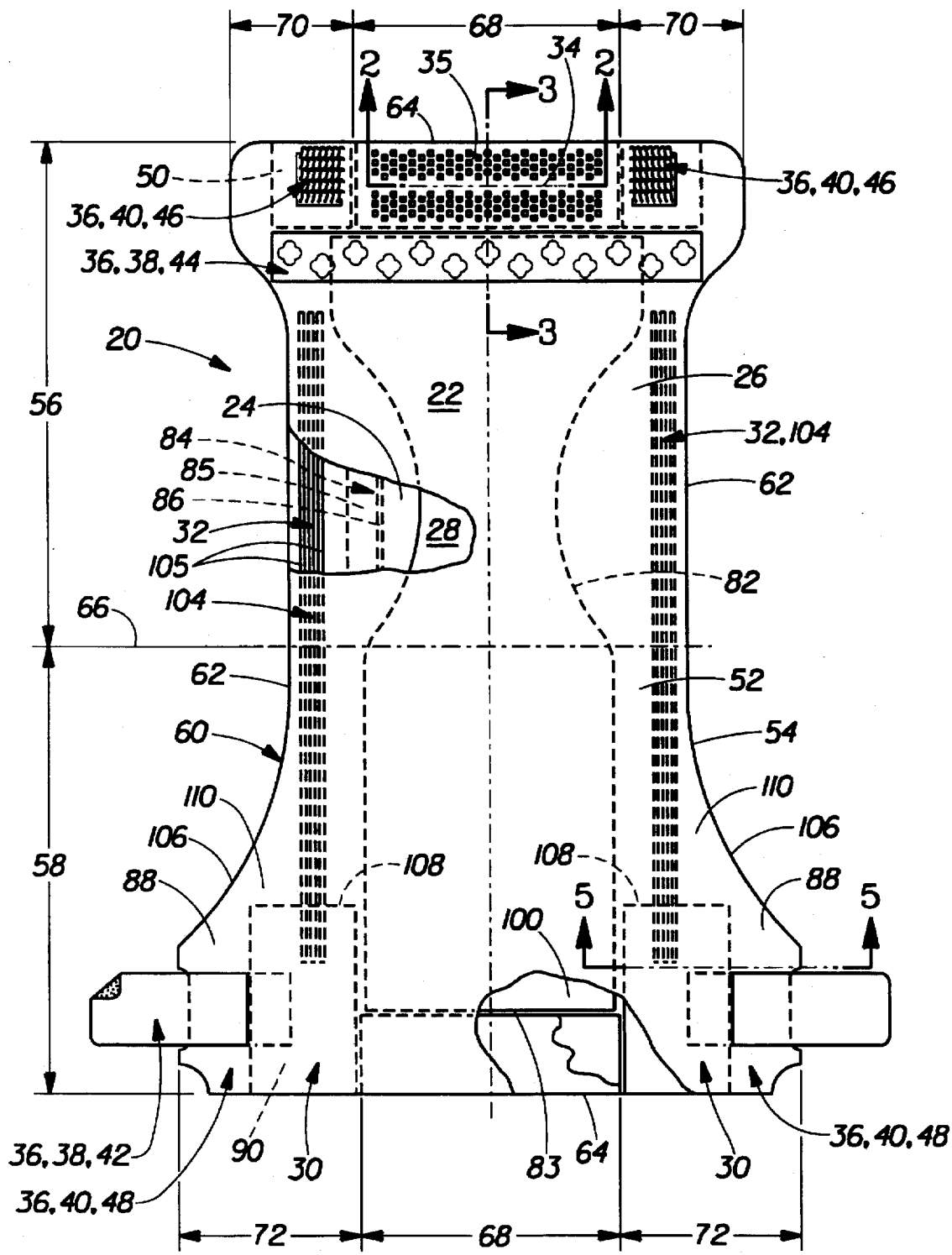
FIG. 1 is a plan view of a disposable diaper embodiment of the present invention having portions cut-away to reveal underlying structure, the outer surface of the diaper facing the viewer.

A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

FIG. 1 is a plan view of the diaper 20 of the present invention in its flat-out, uncontracted state (i.e., with elastic induced contraction pulled out except in the side panel wherein the elastic is left in its relaxed condition) with portions of the structure being cut-away to more clearly show the construction of the diaper 20 and with the portion of the diaper 20 which faces away from the wearer, the outer surface 52, oriented towards the viewer. As shown in FIG. 1, the diaper 20 comprises a containment assembly 22 preferably comprising a liquid pervious topsheet 24; a liquid impervious backsheet 26 joined with the topsheet 24; an absorbent core 28 positioned between the topsheet 24 and the backsheet 26; elasticized side panels 30; elasticized leg cuffs 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46.

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. (While one skilled in the art will recognize that a diaper is usually described in terms of having a pair of waist regions and a crotch region between the waist regions; in this application, for simplicity and terminology, the diaper 20 is described as having only waist regions, each of the waist regions including a portion of the diaper which would typically be designated as part of the crotch region.) The inner surface 54 of the diaper 20 comprises that portion of the diaper 20 which is positioned adjacent to the wearer's body during use (i.e., the inner surface 54 generally is formed by at least a portion of the topsheet 24 and other components joined to the topsheet 24). The outer surface 52 comprises that portion of the diaper 20 which is positioned away from the wearer's body (i.e., the outer surface 52 generally is formed by at least a portion of the backsheet 26 and other components joined to the backsheet 26).

The first waist region 56 and the second waist region 58 extend, respectively, from the end edges 64 of the periphery 60 to the lateral centerline 66 of the diaper 20. The waist regions each comprise a central region 68 and a pair of side panels which typically comprise the outer lateral portions of the waist regions. The side panels positioned in the first waist region 56 are designated 70 while the side panels and the second waist region 58 are designated 72. (In the discussion the follows, unless otherwise noted, the diaper 20 will comprise a pair of side panels in each waist region. While it is not necessary that the pairs of side panels be identical, they are preferably mirror images one of the other.) In a preferred embodiment of the present invention, the side panels 72 positioned in the second waist region 58 are elastically extensible in a lateral direction (i.e., elasticized side panels 30). (The lateral direction (x direction or width) is defined as the direction parallel to the lateral center line 66 of the diaper 20; the longitudinal direction (y direction or length) being defined as the direction parallel to the longitudinal center line 67; and the axial direction (z direction or thickness) being defined as the direction extending through the thickness of the diaper 20.)

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and the end edges 64.

Figure 2:
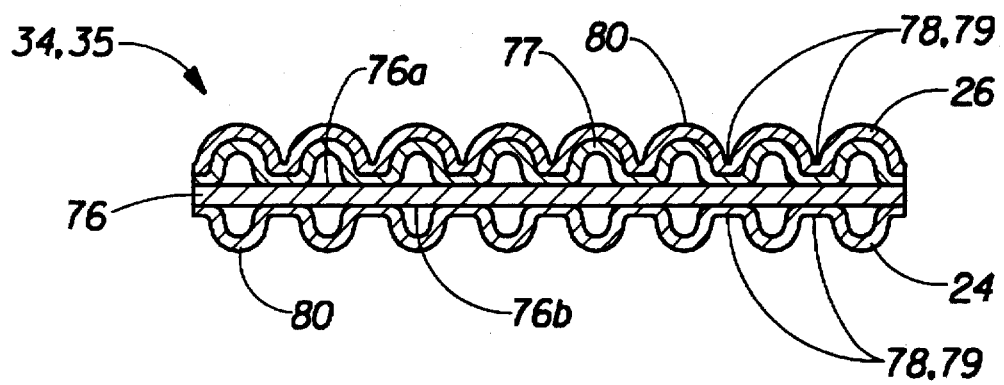
FIG. 2 is a fragmentary sectional view of the disposable diaper shown in FIG. 1 taken along section line 2—2 of FIG. 1.

FIG. 2 is a cross-sectional view of the diaper 20 taken along section line 2—2 of FIG. 1 in the first waist region 56. FIG. 2 shows the construction of the elasticized waistband 35 of the elastic waist feature 34. The elasticized waistband 35 is shown in FIG. 2 in its contracted or relaxed condition. The elasticized waistband 35 preferably comprises a portion of the topsheet 24, a portion of the backsheet 26, and a composite member comprising an elastomeric member 76 and a three-dimensional, macroscopically expanded, formed-film member 77. The elasticized waistband 35 is also provided with regions of securement 78 wherein the backsheet 26 and the topsheet 24 are joined to the composite member. Since the topsheet 24 and the backsheet 26 are gathered when the composite member is in its relaxed condition, regions of differential securement are provided which form pleats 80.

Figure 3:
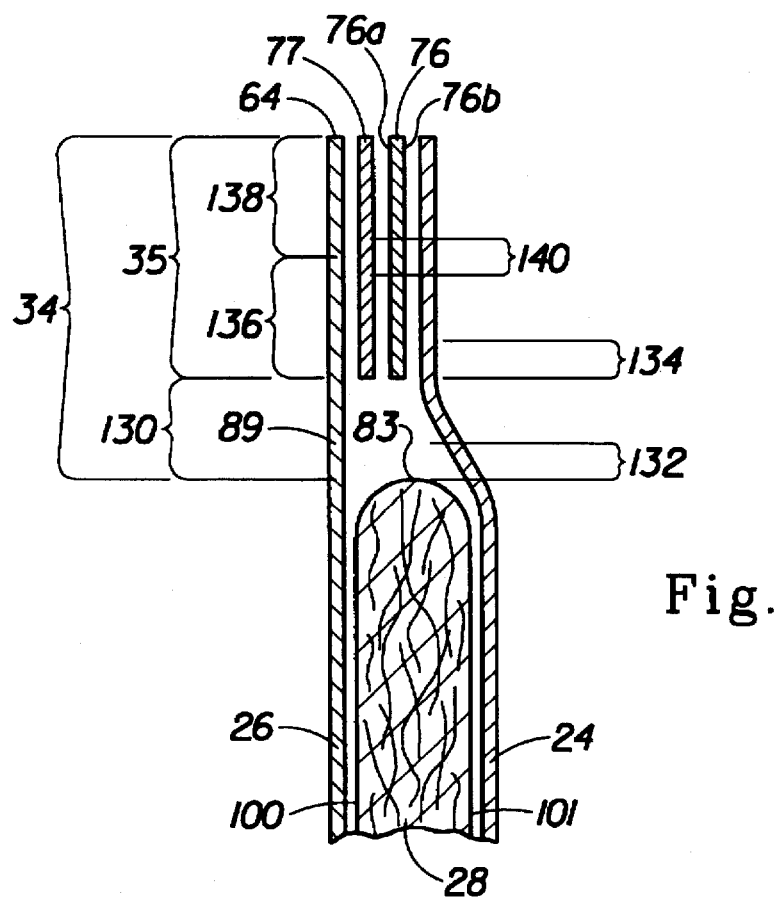
FIG. 3 is a fragmentary sectional view of the disposable diaper shown in FIG. 1 taken along section line 3—3 of FIG. 1.

FIG. 3 is a fragmentary cross-sectional view of the diaper 20 taken along section line 3—3 of FIG. 1. The absorbent core 28 is generally shown in FIG. 3 and shows the waist edge 83 of the absorbent core 28. The topsheet 24 and the backsheet 26 encase the absorbent core 28 and extend longitudinally outwardly beyond the waist edge 83 of the absorbent core 28 to form a waist flap 89 and the end edge 64. The elastic waist feature 34 extends longitudinally outwardly from the waist edge 83 of the absorbent core 28 in at least the central region 68 and forms at least a portion of the end edge 64. The elastic waist feature 34 comprises an interconnecting panel zone 130, a first flexural hinge zone 132 joining the interconnecting panel zone 130 with the containment assembly 22 adjacent the waist edge edge 83 of the absorbent core 28, an elasticized waistband 35, and a second flexural hinge zone 134. The elasticized waistband comprises a shaping panel zone 136, a waistline panel zone 138, a predisposed, resilient, waistband flexural hinge zone 140 joining the shaping panel zone 136 and the waistline panel zone 138. The interconnecting panel zone 130 comprises a portion of the topsheet 24 and the backsheet 26 while the elasticized waistband comprises a portion of the topsheet 24 and the backsheet 26 and the composite member.

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface 100, a body surface 101, side edges 82, and waist edges 83.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. Exemplary absorbent structures for use as the absorbent core 28 are described in U.S. Pat. No. 4,610,678 issued to Weisman et al. on Sep. 9, 1986; U.S. Pat. No. 4,673,402 issued to Weisman et al. on Jun. 16, 1987; U.S. Pat. No. 4,888,231 issued to Angstadt on Dec. 19, 1989; and U.S. Pat. No. 4,834,735 issued to Alemany et al. on May 30, 1989. Each of these patents are incorporated herein by reference.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils).

In a preferred embodiment of the present invention, at least a portion of the backsheet 26 is subjected to mechanical stretching in order to provide both a "zero strain" stretch laminate that forms the elasticized side panels 30 and to prestrain the portion of the backsheet coinciding with the elastic waist feature. Thus, the backsheet 26 is preferably elongatable, most preferably drawable, but not necessarily elastomeric, so that the backsheet 26 will, upon mechanical stretching, be at least to a degree permanently elongated such that it will not fully return to its original undistorted configuration. In preferred embodiments, the backsheet can be subjected to mechanical stretching without undue rupturing or tearing. Thus, it is preferred that the backsheet 26 have an ultimate elongation to break of at least about 400% to about 700% in the cross-machine direction as measured using a method consistent with the ASTM (American Society of Testing Materials) D-638. Thus, preferred polymeric films for use as the backsheet contain a high content of linear low density polyethylene. Particularly preferred materials for the backsheet 26 include blends comprised of about 45-90% linear low density polyethylene and about 10-55% polypropylene. Exemplary films for use as the backsheet include RR8220 blend for blown films and RR5475 blend for cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery 60 and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28.

In a preferred embodiment of the present invention, at least a portion of the topsheet 24 is subjected to mechanical stretching in order to provide a "zero strain" stretch laminate that forms the elasticized side panels 30. Thus, the topsheet 24 is preferably elongatable, most preferably drawable, but not necessarily elastomeric, so that the topsheet 24 will, upon mechanical stretching, be at least to a degree permanently elongated such that it will not fully return to its original configuration. In preferred embodiments, the topsheet 24 can be subjected to mechanical stretching without undue rupturing or tearing of the topsheet. Thus, it is preferred that the topsheet 24 have a low cross-machine direction (lateral direction) yield strength.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 issued to Aziz et al. on Mar. 20, 1990, describes a disposable diaper having "stand-up" elasticized flaps (barrier cuffs) to improve the containment of the leg regions. U.S. Pat. No. 4,695,278 issued to Lawson on Sep. 22, 1987, describes a disposable diaper having dual cuffs including a gasketing cuff and a barrier cuff. U.S. Pat. No. 4,704,115 issued to Buell on Nov. 3, 1987, discloses a disposable diaper or incontinent garment having side-edge-leakage-guard gutters configured to contain free liquids within the garment. Each of these patents are incorporated herein be reference. While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in the above-referenced U.S. Pat. No. 4,909,803. In a preferred embodiment, the elasticized leg cuff 32 additionally comprises an elastic gasketing cuff 104 with one or more elastic strands 105, positioned outboard of the barrier cuff 84 such as described in the above-referenced U.S. Pat. No. 4,695,278.

The diaper 20 preferably further comprises an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region, although diapers can be constructed with a single elastic waist feature. Further, while the elastic waist feature or any of its constituent elements can comprise a separate element affixed to the containment assembly 22 of the diaper 20, the elastic waist feature 34 will be described with respect to a preferred embodiment in which the elastic waist feature 34 is constructed as an extension of other elements of the diaper such as the backsheet 26 or the topsheet 24, preferably both the backsheet 26 and the topsheet 24.

While the elastic waist feature 34 need only comprise an elasticized waistband and a flexural hinge zone joining the elasticized waistband with the containment assembly; as shown in FIG. 3, the elastic waist feature 34 preferably comprises several additional zones. In particular, the elastic waist feature 34 comprises an interconnecting panel zone 130, a first flexural hinge zone 132 joining the interconnecting panel zone 130 with the containment assembly 22 adjacent the waist edge 83 of the absorbent core 28, an elasticized waistband 35, and a second flexural hinge zone 134 joining the elasticized waistband 35 with the interconnecting panel zone 130. The interconnecting panel zone 130 preferably provides a flexible link between the elasticized waistband 35 and the containment assembly 22. The elasticized waistband 35 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. As shown in FIG. 3, the elasticized waistband 35 comprises a shaping panel zone 136, a waistline panel zone 138, and a predisposed, resilient, waistband flexural hinge zone 140. A more detailed description of the various zones of the elastic waist feature 34 are described in U.S. Pat. No. 5,151,092 issued to Buell et al. on Sep. 29, 1992, and in U.S. Pat. No. 5,196,000 issued to Clear et al. on Mar. 23, 1993. Each of these patents are incorporated herein by reference.

The elasticized waistband 35 is that portion or zone of the diaper 20 which is intended to elastically expand and contract and to dynamically fit the wearer's waist. The elasticized waistband is preferably formed as an extension of the topsheet 24 or the backsheet 26, and, most preferably, the topsheet 24 and the backsheet 26. The elasticized waistband 35 is preferably that portion of the elastic waist feature 33 extending from the second flexural hinge zone 134 to, preferably but not necessarily, the end edge 64 of the diaper 20.

In a preferred embodiment, as shown in FIG. 2, the elasticized waistband 35 preferably is constructed from several materials laminated together. The elasticized waistband 35 preferably comprises a portion of the topsheet 24, a portion of the backsheet 26, this portion of the backsheet being preferably "mechanically prestrained", and a composite member comprising an elastomeric member 76 and a three-dimensional, macroscopically expanded, formed-film member 77. The elastomeric member 76 has a first surface 76a and a second surface 76b. The three-dimensional, macroscopically expanded, formed-film member 77 is preferably secured to the first surface 76a of the elastomeric member 76, preferably by dynamic mechanical bonds, prior to being combined with the topsheet 24 and the backsheet 26. During bonding of the three-dimensional, macroscopically expanded, formed-film member 77 to the elastomeric member 76, apertures may be formed in the elastomeric member 76 when ultrasonically or mechanically bonded. The composite member is preferably positioned between the topsheet 24 and the backsheet 26 with the three-dimensional, macroscopically expanded, formed-film member 77 disposed toward the backsheet 26 and the elastomeric member 76 disposed toward the topsheet 24.

The elasticized waistband may comprise a portion of the topsheet, a portion of the backsheet, and a composite member comprising an elastomeric member, and two three-dimensional, macroscopically expanded, formed-film members. The elastomeric member is preferably sandwiched between and secured to the two three-dimensional, macroscopically expanded, formed-film members along the first surface and the second surface of the elastomeric member, respectively, to form a composite member prior to being combined with the topsheet and the backsheet.

Alternatively, the elasticized waistband may comprise a portion of the topsheet, a portion of the backsheet, and a composite member comprising an elastomeric member, a three-dimensional, macroscopically expanded, formed-film member and a nonwoven web. Preferably, the three-dimensional, macroscopically expanded, formed film member is secured to the first surface of the elastomeric member and the nonwoven web is secured to the second surface of the elastomeric member to form a composite member prior to being combined with the topsheet and the backsheet.

The elastomeric member 76 is operatively associated with the elasticized waistband 35, preferably between the topsheet 24 and the backsheet 26, so that the elastomeric member 76 allows the elasticized waistband 35 to be elastically extensible in the lateral direction, and so that it can contractively return to its substantially unrestrained configuration. The elastomeric member 76 can be operatively associated in the elasticized waistband 35 in a number of different ways. As an example, the elastomeric member may be operatively associated in an elastically contractible condition so that the elastomeric member gathers or contracts the elasticized waistband. (A more detailed description of the manner in which elastomeric materials may be secured in absorbent article in an elastically contractible condition can be found in U.S. Pat. No. 3,860,003 issued to Buell on Jan. 14, 1975, and in U.S. Pat. No. 4,081,301 issued to Buell on Mar. 28, 1978; both patents being incorporated herein by reference.) For example, the elastomeric members 76 can be contractibly affixed in the elasticized waistband 35 by laterally extending the elastomeric member 76, affixing the elastomeric member 76 to the three-dimensional, macroscopically expanded, formed-film member 77 and allowing the elastomeric member 76 to assume its relaxed or contracted orientation.

Alternatively, the elastomeric member 76 can be operatively associated in the elasticized waistband 35 by securing the elastomeric member 76 to the three-dimensional, macroscopically expanded, formed-film member 77, while the elastomeric member 76 is in a substantially untensioned condition, at least a portion of the laminate containing the elastomeric member can then be subjected to mechanical stretching sufficient to permanently elongate the topsheet 24, the backsheet 26, and the three-dimensional, macroscopically expanded, formed-film member 77, and then the laminate is returned to its substantially untensioned condition. The elasticized waistband is thus formed into a "zero strain" stretch laminate. (As discussed hereinafter, the elastomeric laminate may alternatively be operatively associated in a tensioned condition and subjected to mechanical stretching to form a mechanically stretched, pretensioned, stretch laminate.)

In an especially preferred embodiment, the elastomeric member 76 can be operatively associated in an uncontracted state and then treated to contract. In this embodiment, the elastomeric member 76 can be formed from materials which contract unidirectionally and become elastic following specific treatment such as heating. Examples of such materials are disclosed in U.S. Pat. No. 3,819,401 issued to Massengale, et al. on Jun. 25, 1974 and in U.S. Pat. No. 3,912,565 issued to Koch, et al. on Oct. 14, 1975. A more detailed description of a manner for using a heat-shrinkable elastomeric member is described in U.S. Pat. No. 4,515,595 issued to Kievit et al. on May 7, 1985; this patent being incorporated herein by reference. Typically, the elastomeric member 76 and the three-dimensional, macroscopically expanded, formed-film member 77, are secured together while in an uncontracted condition. The composite is then heated and the elastomeric member 76 is allowed to return to its relaxed or contracted condition.

The elastomeric member of the present invention may take on a number of different sizes, shapes, configurations, and materials. Materials which have been found suitable for use as the elastomeric member include "live" synthetic or natural rubber, elastomeric films (including heat-shrinkable elastomeric films), formed elastomeric scrim, or the like.

The three-dimensional, macroscopically expanded, formed-film member 77 provides enhanced shape recovery and bending stiffness to the elasticized waistband 35. The three-dimensional, macroscopically expanded, formed-film member 77 provides compression/buckling resistance in the longitudinal direction so that the waistband flexural hinge zone 140 will be resilient so as to provide a restoring force/moment. The three-dimensional, macroscopically expanded, formed-film member 77 also has a relatively high caliper to provide Z-direction bulk to the elasticized waistband 35 to optimize its resiliency.

While the three-dimensional, macroscopically expanded, formed-film member 77 is preferably positioned between the elastomeric member 76 and the backsheet 26, the three-dimensional, macroscopically expanded, formed-film member 77 may alternatively be positioned between the topsheet 24 and the elastomeric member 76. The three-dimensional, macroscopically expanded, formed-film member 77 is preferably positioned between the backsheet 26 and the elastomeric member 76 to provide greater compression/buckling resistance on the backsheet side of the elasticized waistband. A three-dimensional, macroscopically expanded, formed-film member 77 may alternatively be positioned on both sides of the elastomeric member 76, i.e., the elastomeric member 76 is sandwiched between two three-dimensional, macroscopically expanded, formed-film members 77. In another preferred embodiment, the elastomeric member 76 may be sandwiched between a three-dimensional, macroscopically expanded, formed-film member 77 and a nonwoven web.

Figure 4:
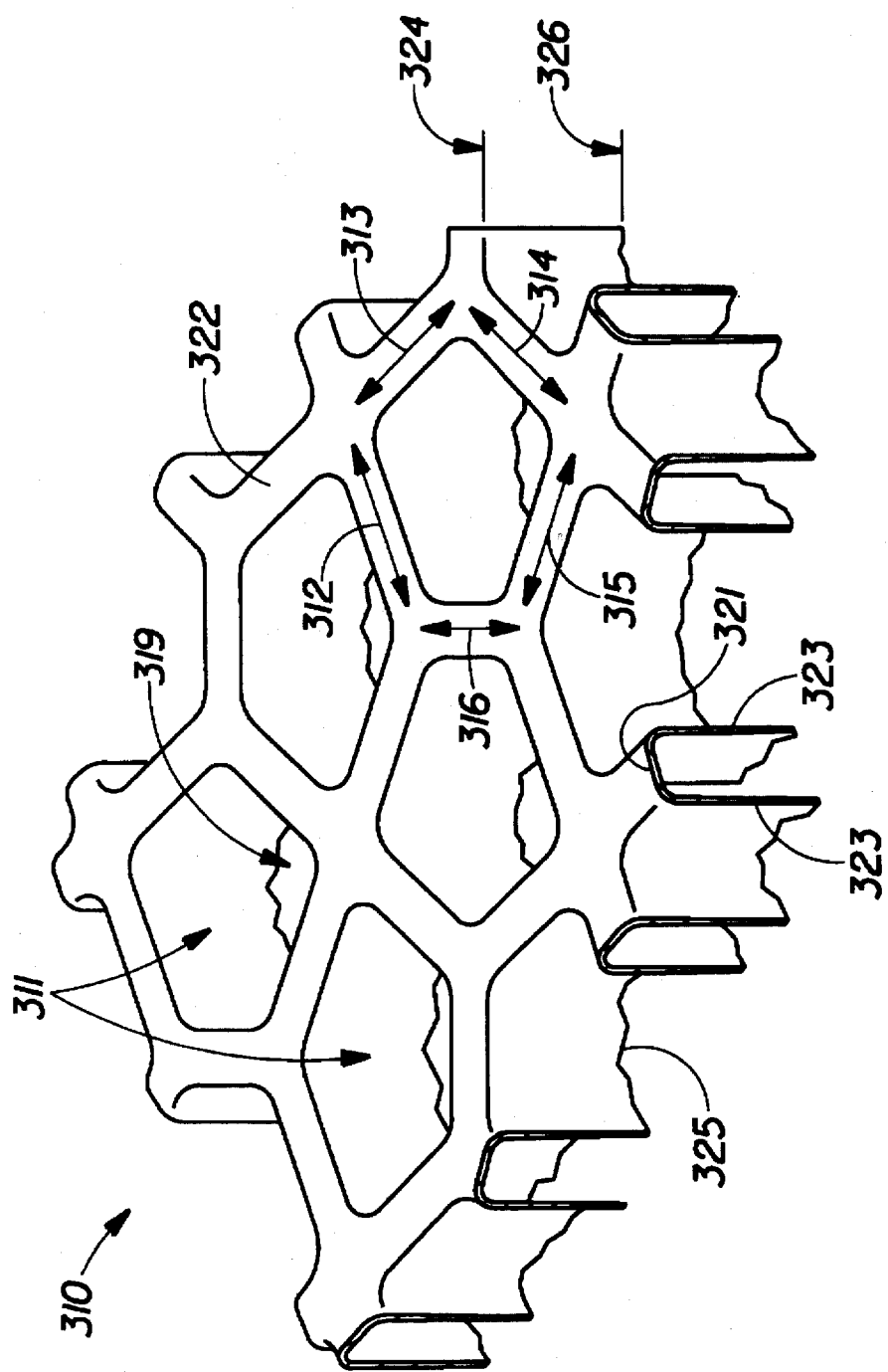
FIG. 4 is a segmented perspective illustration of a three-dimensional, macroscopically expanded, formed-film.

Exemplary three-dimensional, macroscopically expanded, formed-films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference. FIG. 4 is an enlarged, partially segmented, perspective illustration of a three-dimensional, macroscopically expanded, fiber-like, formed-film 310 which has been found highly suitable for use as the three-dimensional, macroscopically expanded, formed-film member 77. The formed-film 310 is generally in accordance with the teachings of commonly assigned U.S. Pat. No. 4,342,314. The formed-film 310 illustrated in FIG. 4 exhibits a multiplicity of apertures, e.g., apertures 311, which are formed by a multiplicity of intersecting fiber-like elements, e.g., elements 312, 313, 314, 315 and 316 interconnected to one another in the first surface 322 of the web. Each fiber-like element comprises a base portion, e.g., base portion 321, located in plane 324. Each base portion has a side wall portion, e.g., side wall portions 323, attached to each edge thereof. The side wall portions extend generally in the direction of the second surface 325 of the web. The intersecting side wall portions of the fiber-like elements are inner connected to one another intermediate the first and second surfaces of the web, and terminate substantially concurrently with one another in the plane 326 of the second surface 325.

In a particularly preferred embodiment, the interconnected side wall portions terminate substantially concurrently with one another in the plane of the second surface to form apertures 319 in the second surface 325 of the web. However, it is not critical that apertures 319 be formed in the second surface of the formed-film as this material will not be critical to the passage or blockage of fluids absorbed or transmitted by the disposable diaper 20. For example, the material may be debossed.

As can be seen in FIG. 4 the formed-film provides a significant amount of bulk or caliper as compared to the thickness of the material used to form the formed-film. As such, the formed-film has a high degree of resiliency. Furthermore, when secured to the elastomeric member 76 the formed-film 77 provides the elasticized waistband with a significant degree of stiffness.

In a preferred embodiment, the portion of the backsheet 26 forming the elasticized waistband may be "prestrained" or "mechanically prestrained" (i.e., subjected to some degree of localized pattern of mechanical stretching to permanently elongate those portions of the backsheet forming the elasticized waistband 35). A more detailed description of prestraining is disclosed in U.S. Pat. No. 5,151,092 issued to Buell et al. on Sep. 29, 1992, and in U.S. Pat. No. 5,196,000 issued to Clear et al. on Mar. 23, 1993; each of these patents being incorporated herein by reference.

In a preferred method for making the diapers of the present invention, after the backsheet has been prestrained, a continuous spray of glue is applied to the backsheet. The composite comprising the three-dimensional, macroscopically expanded, formed-film member 77 and the elastomeric member 76 is dynamically mechanically bonded with the topsheet. The resulting topsheet/elastomeric member/three-dimensional, macroscopically expanded formed-film laminate is then applied to the prestrained backsheet and dynamically mechanically bonded together to from the elasticized waistband.

The elasticized waistband 35 further comprises transverse regions of securement 78 shown in FIG. 2. The transverse regions of securement 78 are shown as discrete, spaced, securement zones 79 effectively attaching the webs of material forming the elasticized waistband 35 (the topsheet 24, the backsheet 26, the elastomeric member 76, and the three-dimensional, macroscopically expanded, formed-film member 77) together. A more detailed description of the transverse regions of securement and alternative configurations for them are found in U.S. Pat. No. 4,515,595 issued to Kievit et al. on May 7, 1985; U.S. Pat. No. 5,151,092 issued to Buell et al. on Sep. 29, 1992, and in U.S. Pat. No. 5,196,000 issued to Clear et al. on Mar. 23, 1993; each of these patents being incorporated herein by reference.

In an alternative embodiment, the elasticized waistband in the second waist region 58 (or the first waist region if elasticized side panels are disposed therein) and the elasticized side panels 30 can be formed by securing a single piece of composite material comprising an elastomeric member and a three-dimensional, macroscopically expanded, formed-film member, to the diaper 20 in both the side panels 72 and the central region 68 of the second waist region 58. Thus, the elasticized waistband 35 and the elasticized side panels 30 can be formed from the same composite material.

The diaper 20 is also preferably comprised with a closure system (tensioning means) for dynamically creating/maintaining lateral tension through the elasticized waistband 35. While the closure system may take on a number of configurations such as adhesive tape tabs, mechanical closure tape tabs, fixed position fasteners, or any other means for tensioning the elasticized waistband as are known in the art; as shown in FIG. 1, the closure system preferably comprises a waist closure system 40 comprising at least one, typically a pair of, first attachment components 46 and at least one second attachment component 48. More preferably, the closure system additionally comprises a primary fastening system 38 such that the diaper 20 has a dual tension fastening system 36. Preferred embodiments of a diaper having a dual tension fastening system are described in U.S. patent application, Ser. No. 07/714,476, Weil et al. now U.S. Pat. No. 5,242,436. "Absorbent Article With Fastening System Providing Dynamic Elasticized Waistband Fit", the specification and drawing of which are incorporated herein by reference.

In a preferred embodiment, the diaper also comprises elasticized side panels 30 disposed in the second waist region 58. (As used herein, the term "disposed" is used to mean that an element(s) of the diaper is formed (joined and positioned) in a particular place or position as a unitary structure with other elements of the diaper or as a separate element joined to another element of the diaper.) The elasticized side panels 30 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. The elasticized side panels 30 further provide more effective application of the diaper 20 since even if the diaper pulls one elasticized side panel 30 farther than the other during application (asymmetrically), the diaper 20 will "self-adjust" during wear. While the diaper 20 of the present invention preferably has the elasticized side panels 30 disposed in the second waist region 58; alternatively, the diaper 20 may be provided with elasticized side panels 30 disposed in the first waist region 56 or in both the first waist region 56 and the second waist region 58.

The elasticized side panel 30 preferably comprises an ear flap 88 and a composite elastic side panel member 90 associated therewith. As shown in FIG. 1, each ear flap 88 comprises that portion of the side panel 72 that extends laterally outwardly from and along the side edge 82 of the absorbent core 28 to the longitudinal edge 62 of the diaper 20. The ear flap 88 generally extends longitudinally from the end edge 64 of the diaper 20 to the portion of the longitudinal edge 62 of the diaper 20 that forms the leg opening (this segment of the longitudinal edge 62 being designated as leg edge 106). In a preferred embodiment of the present invention, each ear flap 88 in the second waist region 58 is formed by the portions of the topsheet 24 and the backsheet 26 that extend beyond the side edge 82 of the absorbent core 28.

In a preferred embodiment of the present invention, the composite elastic side panel members 90 are operatively associated with the diaper 20 in the ear flaps 88, preferably between the topsheet 24 and the backsheet 26, so that the composite elastic side panel members 90 allow the elasticized side panels 30 to be elastically extensible in the lateral direction (laterally elastically extensible). As used herein, the term "elastically extensible" means a segment or portion of the diaper that will elongate in at least one direction (preferably the lateral direction for the side panels and the waistbands) when tensional forces (typically lateral tensional forces for the side panels and the waistbands) are applied, and will return to about its previous size and configuration when the tensional forces are removed. Generally, composite elastomeric materials useful in the present invention will contractively return to at least about 75% of their original configuration within about 5 seconds or less upon stretch and immediate release thereof (i.e., a "snappy" elastic).

Figure 5:
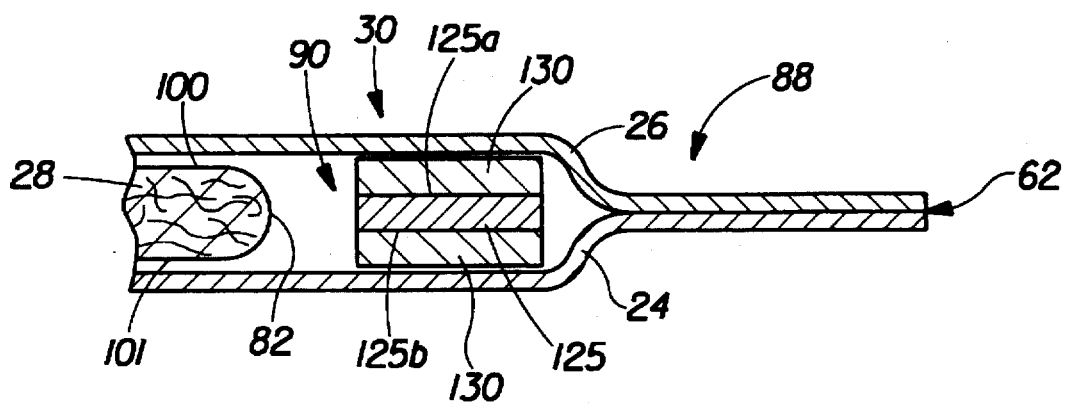
FIG. 5 is a fragmentary sectional view of the disposable diaper shown in FIG. 1 taken along section line 5—5 of FIG. 1.

The composite elastic side panel members 90 preferably comprise a composite of two or more materials. As can be seen in FIG. 5 the composite elastic side panel member 90 preferably comprises a central elastomeric member 125 and two three-dimensional, macroscopically expanded, formed-film members 130. The elastomeric member 125 has a first surface 125a and a second surface 125b. The elastomeric member 125 is preferably sandwiched between and secured to the two three-dimensional, macroscopically expanded, formed-film members 130 along the first surface 125a and the second surface 125b of the elastomeric member 125 to form a composite member 90 prior to being combined with the topsheet 24 and the backsheet 26.

The composite 90 may comprise an elastomeric member and one three-dimensional, macroscopically expanded, formed-film member secured to the first surface thereof. Alternatively, the composite 90 may comprise an elastomeric member, a three-dimensional, macroscopically expanded, formed-film member, and a nonwoven web. Preferably, the macroscopically expanded, formed-film member is secured to the first surface of the elastomeric member, and the nonwoven web is secured to the second surface of the elastomeric member.

Materials which have been found suitable for the elastomeric member include "live" synthetic or natural rubber, elastomeric films (including heat-shrinkable elastomeric films), formed elastomeric scrim, or the like.

Exemplary three-dimensional, macroscopically expanded, formed-films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference. FIG. 4 is an enlarged, partially segmented, perspective illustration of a particularly preferred three-dimensional, fiber like, fluid pervious formed film which has been found highly suitable for use as the three-dimensional, macroscopically expanded, formed-film member 130.

The composite elastic side panel members 90 can be operatively associated in the ear flaps 88 in a number of different ways. For example, the composite elastic side panel member 90 may be operatively associated in an elastically contractible condition so that the composite elastic side panel member 90 gathers or contracts the ear flap 88. (A more detailed description of a manner in which elastomeric materials may be secured in an elastically contractible condition can be found in U.S. Pat. No. 3,860,003 issued to Buell on Jan. 14, 1975, and in U.S. Pat. No. 4,081,301 issued to Buell on Mar. 28, 1978; both patents being incorporated herein by reference.) For example, the composite elastic side panel members 90 can be contractibly affixed in the ear flap 88 by laterally extending the composite elastic side panel member 90, joining the composite elastic side panel member 90 to either or both the topsheet 24 and the backsheet 26, and allowing the composite elastic side panel member 90 to assume its relaxed or contracted orientation.

Alternatively, the composite elastic side panel member 90 can be operatively associated in an uncontracted state and then treated to contract. For example, the elastomeric member 125 of the composite elastic side panel member 90 can be formed from materials which contract unidirectionally and become elastic following specific treatment such as heating. Examples of such material are disclosed in U.S. Pat. No. 3,819,401 issued to Massengale, et al. on Jun. 25, 1974 and in U.S. Pat. No 3,912,565 issued to Koch, et al. on Oct. 14, 1975. A more detailed description of a manner for using a heat-shrinkable elastomeric film is described in U.S. Pat. No. 4,515,595 issued to Kievit et al. on May 7, 1985; this patent being incorporated herein by reference.

In an especially preferred embodiment, the composite elastic side panel member 90 is operatively associated in the ear flap 88 by joining the composite elastic side panel member 90 to the topsheet 24, the backsheet 26, or both while the composite elastic side panel member 90 is in a substantially untensioned condition. At least a portion of the resultant elasticized side panel containing the composite elastic side panel member 90 is then subjected to mechanical stretching sufficient to permanently elongate all nonelastic components of the elasticized side panel. The elasticized side panel is then allowed to return to its substantially untensioned condition. The elasticized side panel is thus formed into a "zero strain" stretch laminate. (Alternatively, the composite elastic side panel member could be operatively associated in a tensioned condition and then subjected to mechanical stretching; although this is not as preferred as a "zero strain" stretch laminate.) As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., it will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting "zero strain" stretch laminate is thereby rendered elastically extensible, at least up to the point of initial stretching, in the direction of initial stretching. Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; and U.S. Pat. No. 4,834,741 issued to Sabee on May 30, 1989. Each of these patents are incorporated herein by reference.

Particularly preferred methods and apparatus used for making "zero strain" stretch laminates out of a topsheet, a backsheet, and an elastomeric member positioned between the same, use meshing corrugated rolls to mechanically stretch the components. A discussion of suitable apparatus and methods for mechanically stretching portions of a diaper is contained in the hereinbefore referenced U.S. Pat. No. 4,107,364 issued to Sisson on Aug. 15, 1978 and U.S. Pat. No. 4,834,741 issued to Sabee on May 30, 1989. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1992; and U.S. Pat. No. 5,143,679 issued to Weber et al. on Sep. 1, 1992; each one being incorporated herein by reference.

The composite elastic side panel members 90 can be joined to either the topsheet 24, the backsheet 26, or both using either an intermittent bonding configuration or a substantially continuous bonding configuration. As used herein, an "intermittently" bonded laminate web means a laminate web wherein the plies are initially bonded to one another at discrete spaced apart points or a laminate web wherein the plies are substantially unbonded to one another in discrete spaced apart areas. Conversely, a "substantially continuously" bonded laminate web means a laminate web wherein the plies are initially bonded substantially continuously to one another throughout the areas of interface. The intermittent bonding configuration is normally desirable for "zero strain" laminate webs in those situations where the substantially inelastic webs in the laminate are relatively elongatable or drawable without rupture and where a high degree of z-direction bulking is desired in the finished laminate. A continuous bonding configuration has generally been found desirable for "zero strain" laminate webs where the degree of z-direction bulking of the finished laminate is not of prime importance and one or more of the relatively inelastic webs in the laminate is difficult to elongate or draw without causing rupture. In the latter situation, a substantially continuous bonding configuration maintains all of the layers of the laminate in relatively close adherence to one another after the incremental stretching operation. Accordingly, even if one or more of the relatively inelastic webs is damaged to the point of rupture during the incremental stretching operation, the relatively close adherence of the damaged portions of the relatively inelastic web or webs to the elastomeric ply makes it difficult for the end user to perceive that any damage has occurred. Provided that the rupture of the relatively inelastic web or webs does not defeat the web's intended functionality, (e.g., imperviousness), the damage which does occur to the relatively inelastic web or webs during the incremental stretching operation is generally not perceived as a negative in the end product.

Thus, an unexpected benefit which results from the use of a continuous bonding configuration in particularly preferred "zero strain" stretch laminate webs is that it permits the manufacturer of the diaper to select from a much wider range of relatively inelastic webs which may be successfully employed in laminates of the present invention. In essence, it permits the use of relatively inelastic webs which would not normally be considered drawable to any appreciable extent in "zero strain" stretch laminate webs of the present invention. Accordingly, unless expressly stated otherwise, the term "drawable" as used herein, is not intended to exclude relatively inelastic webs which undergo a degree of thinning or damage during the incremental stretching operation.

In a preferred embodiment of the present invention, the composite elastic side panel member 90 is substantially continuously bonded to both the topsheet 24 and the backsheet 26 using an adhesive. A glue applicator may be used to apply a substantially uniform and continuous layer of adhesive to the backsheet 26 and/or the composite topsheet 24 in those predetermined areas where the substantially untensioned elastic side panel member 90 will be placed. In a particularly preferred embodiment, the adhesive selected is stretchable and the glue applicator comprises a melt blown applicating system.

One such melt blown adhesive applicating system which has been found to be particularly well suited for producing a substantially continuously bonded "zero strain" stretch laminate web is a melt blown spray applicator Model No. GM-50-2-1-GH, as available from J&M Laboratories of Gainesville, Ga. The latter system employs a nozzle having 20 orifices per lineal inch, as measured in the cross-machine direction, each orifice measuring approximately 0.020 inches in diameter. A Findley H-2176 Hot Melt Adhesive, as available from Findley Adhesives of Elm Grove, Wis. is preferably heated to a temperature of approximately 340° F. and applied to the backsheet and/or the topsheet at a rate of approximately 7.5–10 milligrams per square inch. Heated compressed air at a temperature of approximately 425° F. and a pressure of approximately 50 psig is issued through the secondary orifices in the adhesive nozzle to assist in uniformly distributing the adhesive fibrils during the laydown operation.

The intimate contact of the hot adhesive with the backsheet 26 for the time which passes prior to the incremental stretching of the resultant "zero strain" stretch laminate portion of the diaper provides softening of the backsheet 26. For some webs, such as conventional polyethylene backsheet material, this softening has been found beneficial in minimizing damage to the backsheet during the incremental web stretching process. This may be particularly important in situations where the web in question imparts some function, (e.g., impervious), to the diaper.

Alternatively, the composite elastic side panel member 90 and any other components comprising the "zero strain" portions of the diaper 20 may be intermittently or continuously bonded to one another using unheated adhesive, heat bonding, pressure bonding, ultrasonic bonding, dynamic mechanical bonding, or any other method as is known in the art.

While the composite elastic side panel member 90 may longitudinally extend through the entire length of the ear flap 88, it is preferred that the composite elastic side panel member 90 extend through only a portion of the length of the ear flap 88 so as to form an extension panel 110. As shown in FIG. 1, the extension panel 110, the portion of the elasticized side panel longitudinally extending from the base edge 108 of the composite elastic side panel member 90 to the leg edge 106 of the ear flap 88, has also been mechanically stretched at least to a degree to be extensible (i.e., the materials that make up the extension panel 110 have been prestrained or permanently elongated). This "prestrained" extension panel allows this portion of the elasticized side panel to effectively elongate (yield) when the "zero strain" stretch laminate portion of the elasticized side panel is extended, without generating excessive tension forces near the leg regions of the wearer that could cause skin irritation or red marking in the legs. (i.e., Without the "prestrained" extension panel, tensional forces would be concentrated along a line through the extension panel 110 when the elasticized side panel is extended that could indent, rub, or chafe the skin of the wearer.) While there are a number of ways to prestrain the extension panel 110 of the elasticized side panels 30, the extension panel 110 is preferably prestrained in the same manner as the mechanical stretching performed on the "zero strain" stretch laminate portion. While the extension panel 110 of the elasticized side panels 30 may be formed from a number of different materials, in the preferred embodiment shown in FIG. 1, the extension panel 110 is formed from the portions of the topsheet 24 and the backsheet 26 forming the ear flap 88.

The diaper 20 is preferably applied to a wearer by positioning one of the waist regions, preferably the second waist region 58, under the wearer's back and drawing the remainder of the diaper between the wearer's legs so that the other waist region, preferably the first waist region 56, is positioned across the front of the wearer. The tape tabs 92 are then released from the release portion. The elasticized side panel 30 is then wrapped around the wearer, while still grasping the tab portion. The elasticized side panel 30 will typically be extended and tensioned during this operation so as to conform to the size and shape of the wearer. The first fastening system is secured to the outer surface of the diaper to effect a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article, said disposable absorbent article comprising:
   (a) a containment assembly including a liquid pervious topsheet, a liquid impervious backsheet joined with said topsheet, and an absorbent core positioned between said topsheet and said backsheet, said absorbent core having side edges and waist edges;
   (b) an elasticized side panel extending laterally outward from at least one of said side edges of said absorbent core; and
   (c) a composite member extending laterally outward from at least one of said side edges of said absorbent core forming a portion of said elasticized side panel, said composite member including an elastomeric member having a first surface and a second surface and a resilient, three-dimensional, macroscopically expanded, formed-film member secured to said first surface of said elastomeric member, said formed-film member having a first surface and a second surface and exhibiting a multiplicity of apertures formed by a multiplicity of intersecting fiber-like elements interconnected to one another in said first surface of said formed-film member, each of said fiber-like elements having a base portion located in said first surface and side wall portions attached to said base portion and extending generally in the direction of said second surface of said formed-film member, said side wall portions of said fiber-like elements being interconnected to one another intermediate said first and second surfaces of said formed-film member and terminating substantially concurrently with one another in said second surface of said formed film member, said formed film member exhibiting a caliper significantly greater than the thickness of material from which said formed-film member is made and exhibiting a high degree of resiliency, such that said formed-film member imparts a significant degree of stiffness and resilience to said composite member.

2. The absorbent article of claim 1 wherein said composite member includes a three-dimensional, macroscopically expanded, formed-film member secured to said second surface of said elastomeric member.

3. The absorbent article of claim 1 wherein said composite member includes a nonwoven web secured to said second surface of said elastomeric member.

4. The absorbent article of claim 1 wherein said elasticized side panel comprises a portion of said backsheet, a portion of said topsheet, and said composite member.

5. The absorbent article of claim 1 wherein said elastomeric member is a heat-shrinkable elastomeric film.

6. The absorbent article of claim 1 further comprising an elasticized waistband extending longitudinally outward from at least one of said waist edges of said absorbent core.

7. The absorbent article of claim 6, wherein said composite member comprises a first composite member, and wherein said absorbent article further comprises a second composite member extending longitudinally outward from at least one of said waist edges of said absorbent core forming a portion of said elasticized waistband, said second composite member including an elastomeric member having a first surface and a second surface and a three-dimensional, macroscopically expanded, formed-film member secured to said first surface of said elastomeric member.

8. The absorbent article of claim 7 wherein said second composite member includes a three-dimensional, macroscopically expanded, formed-film member secured to said second surface of said elastomeric member.

9. The absorbent article of claim 7 wherein said elasticized waistband comprises a portion of said backsheet, a portion of said topsheet, and said second composite member.

10. A disposable absorbent article, said disposable absorbent article comprising:

(a) a containment assembly including a liquid pervious topsheet, a liquid impervious backsheet joined with said topsheet, and an absorbent core positioned between said topsheet and said backsheet, said absorbent core having side edges and waist edges;

(b) an elasticized waistband extending longitudinally outward from at least one of said waist edges of said absorbent core; and (c) a composite member extending longitudinally outward from at least one of said waist edges of said absorbent core forming a portion of said elasticized waistband, said composite member including an elastomeric member having a first surface and a second surface and a resilient, three-dimensional, macroscopically expanded, formed-film member secured to said first surface of said elastomeric member, said formed-film member having a first surface and a second surface and exhibiting a multiplicity of apertures formed by a multiplicity of intersecting fiber-like elements interconnected to one another in said first surface of said formed-film member, each of said fiber-like elements having a base portion located in said first surface and side wall portions attached to said base portion and extending generally in the direction of said second surface of said formed-film member, said side wall portions of said fiber-like elements being interconnected to one another intermediate said first and second surfaces of said formed-film member and terminating substantially concurrently with one another in said second surface of said formed film member, said formed film member exhibiting a caliper significantly greater than the thickness of material from which said formed-film member is made and exhibiting a high degree of resiliency, such that said formed-film member imparts a significant degree of stiffness and resilience to said composite member.

11. The absorbent article of claim 10 wherein said composite member includes a three-dimensional, macroscopically expanded, formed-film member secured to said second surface of said elastomeric member.

12. The absorbent article of claim 10 wherein said composite member includes a nonwoven web secured to said second surface of said elastomeric member.

13. The absorbent article of claim 10 wherein said elasticized waistband comprises a portion of said backsheet, a portion of said topsheet, and said composite member.

14. The absorbent article of claim 10 wherein said elastomeric member is a heat-shrinkable elastomeric film.

15. The absorbent article of claim 10 further comprising an elasticized side panel extending laterally outward from at least one of said side edges of said absorbent core.

16. The absorbent article of claim 15, wherein said composite member comprises a first composite member, and wherein said absorbent article further comprises a second composite member extending laterally outward from at least one of said side edges of said absorbent core forming a portion of said elasticized side panel, said second composite member including an elastomeric member having a first surface and a second surface and a three-dimensional, macroscopically expanded, formed-film member secured to said first surface of said elastomeric member.

17. The absorbent article of claim 16 wherein said second composite member includes a three-dimensional, macroscopically expanded, formed-film member secured to said second surface of said elastomeric member.

18. The absorbent article of claim 16 wherein said elasticized side panel comprises a portion of said backsheet, a portion of said topsheet, and said second composite member.

19. A composite member comprising an elastomeric member having a first surface and a second surface, and a resilient, three-dimensional, macroscopically expanded, formed-film member secured to said first surface of said elastomeric member, said formed-film member having a first surface and a second surface and exhibiting a multiplicity of apertures formed by a multiplicity of intersecting fiber-like elements interconnected to one another in said first surface of said formed-film member, each of said fiber-like elements having a base portion located in said first surface and side wall portions attached to said base portion and extending generally in the direction of said second surface of said formed-film member, said side wall portions of said fiber-like elements being interconnected to one another intermediate said first and second surfaces of said formed-film member and terminating substantially concurrently with one another in said second surface of said formed-film member, said formed-film member exhibiting a caliper significantly greater than the thickness of material from which said formed-film member is made and exhibiting a high degree of resiliency, such that said formed-film member imparts a significant degree of stiffness and resilience to said composite member, said composite member further includes a three-dimensional, macroscopically expanded, formed-film member secured to said second surface of said elastomeric member.

* * * * *